US006927845B2

(12) United States Patent
Liu

(10) Patent No.: US 6,927,845 B2
(45) Date of Patent: Aug. 9, 2005

(54) INTEGRATED POLARIZATION ANALYZER FOR FIBER TELECOMMUNICATIONS

(76) Inventor: Jian Liu, 305 Easy St., Apt. 10, Mountain View, CA (US) 94043

( * ) Notice: Subject to any disclaimer, the term of this patent is extended or adjusted under 35 U.S.C. 154(b) by 134 days.

(21) Appl. No.: 10/288,353

(22) Filed: Nov. 4, 2002

(65) Prior Publication Data

US 2003/0086076 A1 May 8, 2003

Related U.S. Application Data

(60) Provisional application No. 60/338,824, filed on Nov. 3, 2001.

(51) Int. Cl.[7] .............................................. G01N 21/00
(52) U.S. Cl. ..................................................... 356/73.1
(58) Field of Search ........................... 356/73.1; 398/29, 398/152–159

(56) References Cited

U.S. PATENT DOCUMENTS 5,949,560 A * 9/1999 Roberts et al. ............... 398/29

OTHER PUBLICATIONS

J. Liu, Corner–cube four–detector photopolarimeter, 1997, Optics & Laser Technology, vol. 29, pp. 233–238.*

* cited by examiner

*Primary Examiner*—Tu T. Nguyen
(74) *Attorney, Agent, or Firm*—Bo-In Lin

(57) ABSTRACT

A method is disclosed in this invention for designing an optical polarization analyzer for measuring a state of polarization (SOP) of an optical signal transmitted over a particular range of wavelengths. The method includes a step of selecting a corner cube having a specific input medium refraction index and comprising four triangular surfaces and attaching four optical detectors on each of the four surfaces for sequentially absorbing and then reflecting an incident light from one detector to a next detector wherein said incident light is within the particular range of wavelengths. The method further includes a step of selecting a coating to coat over each of the detectors disposed on each of the four surfaces by selecting a coating material and designing an accurately controlled thickness of each of the coatings for controlling a absorption/reflectance ratio for each of the detectors whereby an optimal sensitivity of photopolarimeter is achieved.

23 Claims, 4 Drawing Sheets

Schenatic diagran of the CCFDP

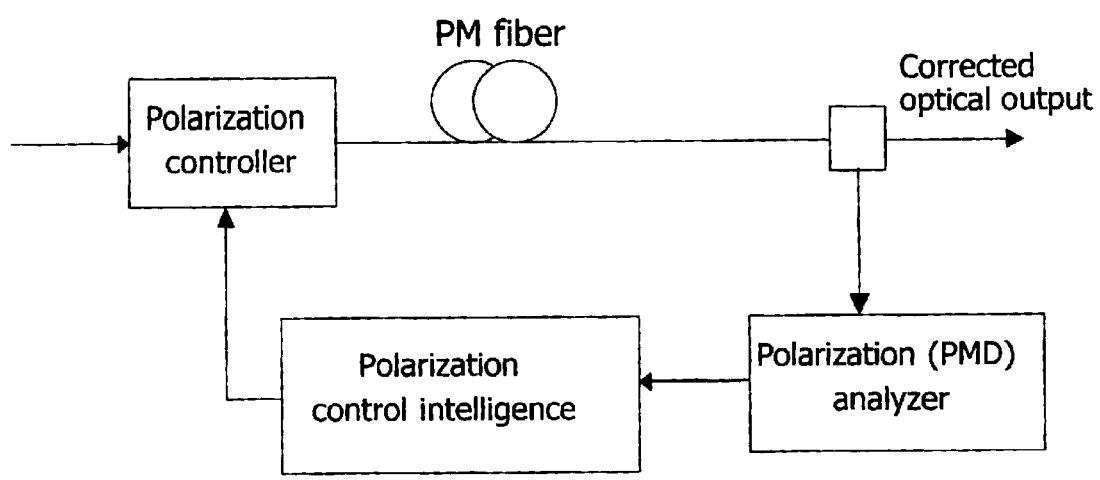
(Prior Art)
Figure 1 A typical setup for PMD compensation

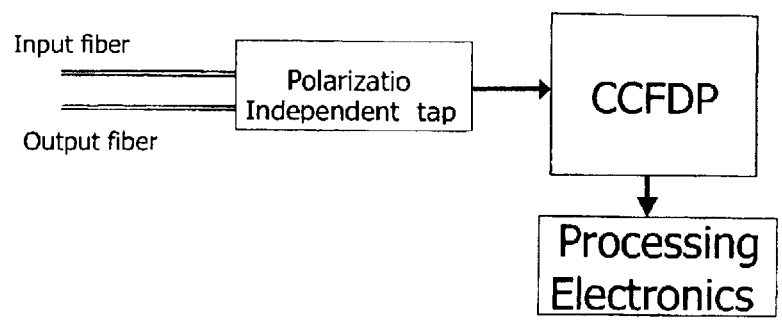
Figure 2  Schematic Diagram of an In-line Polarization Analyzer

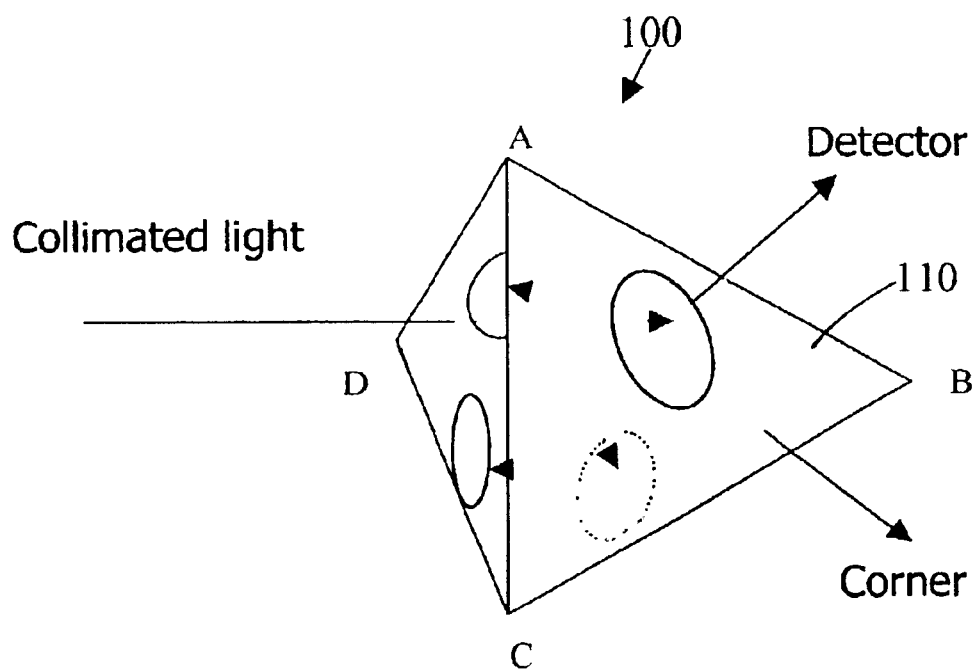
Figure 4 Schenatic diagran of the CCFDP

INTEGRATED POLARIZATION ANALYZER FOR FIBER TELECOMMUNICATIONS This Formal Application claims a Priority Date of Nov. 3, 2001 benefited from a Provisional Application 60/338,824 filed by the same Applicant of this Application on Nov. 3, 2001.

FIELD OF THE INVENTION

The present invention relates generally to apparatuses and method for measuring the state of polarization of a light beam. More particularly, this invention relates to a new configuration for and a method of manufacturing a photopolarimeter for simultaneously measuring all four Stokes parameters defining the state of polarization of a light beam.

BACKGROUND OF THE INVENTION

Conventional technologies in applying a photopolarimeter for measuring the polarization state of a light transmission is faced with the limitations that the manufacture of the photopolarimeters still require manual efforts to align and assemble multiple photodetectors according to predefined optical paths. Furthermore, these multiple photodetectors must maintain at fixed relative positions to achieve reliable and accurate measurements. These requirements may not be easily satisfied when a photopolarimeter is employed to operate under the conditions where the environment may impose humid, heat, vibrations, or other hostile conditions on the photopolarimeters.

In a U.S. Pat. No. 4,681,450 Azzam discloses a photopolarimeter for the simultaneous measurement of all four Stokes parameters of light. The light beam, the state of polarization of which is to be determined, strikes, at oblique angles of incidence, three photodetector surfaces in succession, each of which is partially specularly reflecting and each of which generates an electrical signal proportional to the fraction of the radiation it absorbs. A fourth photodetector is substantially totally light absorbtive and detects the remainder of the light. The four outputs thus developed form a 4×1 signal vector which is linearly related to the input Stokes vector S. Consequently, S is obtained by $S=A^{-1} I$. The 4×4 instrument matrix A is a nonsingular matrix that requires the planes of incidence for the first three detector surfaces are all different. For a given arrangement of four detectors, A can be either computed or determined by calibration. Thus Azzam disclose a configuration for arranging photodetectors to measure the state of polarization (SOP) of a light. However, since the actual implementation of the arrangement of the photodetectors as disclosed would involve manual operations to place these photodetectors at specific locations, practical implementation of the disclosed invention for manufacturing a device for measuring the SOP of a light would not be economically feasible due to a lack of manufacturability.

A configuration of four-detector photopolarimeter using a corner cube configuration was disclosed by Jian Liu and R. M. A. Azzam, "A corner-cube four-detector photopolarimeter," *Optics and Laser Technology* 29(5), 233–238 (1997), and "Polarization properties of corner-cube retroreflectors: theory and experiment," *Applied Optics* 36, 1553–1559 (1997). The disclosures made in these two published papers are hereby incorporated herein as reference of this Application. The disclosures made in these papers however presented further difficulties that the four detectors arranged according to a corner cube configuration cannot be conveniently attached and fixed to the surfaces of the corner cubes without specially designed mechanical structure and well trained alignment skill. On the other hand, the hollow structure requires the detectors positioned in the surfaces of the corner cube further prevent it from minimization of the size of the photopolarimeter.

In the meantime, the demand for mass production of the photopolarimeters is increased, particularly for application in ultra long haul optical transport systems. In the attempts to increase the spectral efficiency by putting similar number of channels (compared with 10 G systems) in one fiber with a date rate of 40 Gbps/channel, and to maintain a competitive price by both keeping the similar or longer distance of transmission without any regenerators, dispersions of multiplexed optical signals over longer distance must be compensated. Innovative technology and manufacturing process to reduce the cost of components and modules such as photopolarimeter for measuring the SOP of light projection to accurately compensate the dispersions are in increased demand. Particularly, the challenges to the implementation of 40-Gbit/sec systems require a broad array of specially developed components and modules. In addition to chromatic dispersion compensation and high-speed electronics, polarization mode dispersion compensation (PMDC) will play an important and essential role in the system implementation. A PMDC device is able to correct the optical signal distortion caused by the degenerate of the two eigen modes of polarization. A PMDC when combined with chromatic dispersion compensation can enable a high date rate of transmission over a long distance. For that reason, a PMDC is usually put in front of a receiver to carry out a channel-by-channel compensation. A typical setup is given in FIG. 1. The polarization controller consists of two quarter wave plates sandwiched with a half wave plate, which their fast axes are rotated to convert any input polarization state into the desired output polarization. A polarization analyzer (photopolarimeter) is an essential module to provide the three control parameters of the rotation angles to fully control the PMD. In order to be suitable for practical and economical system applications, the module of polarization analyzer should be compact, real time, broadband, low cost, and with minimal insertion loss and polarization dependent losses (PDL) for in-line application.

Therefore, a need still exists in the art of manufacturing and designing the polarization analyzer to provide a new configuration to enable the manufacture of a photopolarimeter that is compact, real time responsive, operational over a broadband range, low cost, and with minimal insertion loss and PDL thus suitable for in-line application.

SUMMARY OF THE PRESENT INVENTION

It is therefore an object of the present invention to provide an improved design and configuration for manufacturing and assembling a polarization analyzer that has a compact size, highly reliable and stable configuration integrity, sustainable operation performance over a long term life cycle, and low cost manufacturability such that the above mentioned limitations and difficulties can be resolved.

Specifically, it is an object of the present invention to provide a polarization analyzer formed with four detectors on four surfaces of a solid corner cube where four detectors are attached to the corner cube with specially design coatings composed of material of a specific refraction index and an accurately controlled thickness to achieve optical measurement sensitivity of the detector currents versus the variations of the state of polarization (SOP).

Another object of the present invention is to provide a polarization analyzer with compact size and reliable structure that is suitable of long term reliable implementation in a optical signal transmission system while the polarization analyzer are manufactured with reduced alignment efforts by constructing the analyzer on a corner cube platform such the production cost may be reduced.

Briefly, in a preferred embodiment, the present invention includes a polarization analyzer supported on a corner cube. The polarization analyzer includes four detectors attached on four surfaces of the corner cube for an incident light to project sequentially from one detector to a next detector and absorbing a partial portion of the light projection. Each of the four detectors further includes a costing of predefined optical refraction index and predefined thickness for controlling a reflectance and light absorption for each of these detectors in order to achieve an optimal measurement sensitivity of polarization measurement for a predefined range of light wavelengths.

In a preferred embodiment, this invention further includes an optical signal transmission system. The optical signal transmission system includes an optical tap for tapping a small portion of optical signal from the optical signal transmission system. The optical signal transmission system further includes an inline corner-cube four-detector photopolarimeter (CCFDP) receiving the small portion of optical signal for measuring a state of polarization (SOP) of the optical signal and for generating electric signals corresponding to the SOP. The optical signal transmission system further includes an optical signal processor receiving the electric signals from the CCFDP for generating a polarization mode dispersion compensation signal for the optical signal transmission system. In a preferred embodiment, the CCFDP is a hollowed CCFDP comprising four optical detectors attached to four surfaces constituting a corner cube wherein at least one of surfaces receiving the portion of optical signal to project into the corner cube therein. In another preferred embodiment, the CCFDP is a solid CCFDP composed of optical transmissive material wherein the CCFDP further comprising four optical detectors attached to four surfaces of a corner cube.

These and other objects and advantages of the present invention will no doubt become obvious to those of ordinary skill in the art after having read the following detailed description of the preferred embodiment, which is illustrated in the various drawing figures.

BRIEF DESCRIPTION OF THE DRAWINGS

FIG. 1. is a functional block diagram showing a conventional system configuration for implementing a polarization mode dispersion (PMD) analyzer for polarization mode dispersion compensation (PMCD);

FIG. 2 is a functional block diagram showing the configuration of an inline polarization analyzer of this invention;

FIG. 4 is a schematic diagram showing the configuration of a corner cube four-detector photopolarimeter (CCFDPA) of this invention for inline PMD compensation as that shown in FIG. 2.

DETAILED DESCRIPTION OF THE INVENTION

Referring to FIG. 2 for an inline polarization analyzer of this invention where the corner cube four-detector photopo-larimeter (CCFDP) is integrated with a polarization independent tap. A polarization independent tap couple part of the light out of the optical path without much loss and signal interference added. The tap can be done in free space or with fiber based coupler. A processing electronics is used to convert the detected signals into Stokes parameters representing the state of polarization to generate the control signals for the polarization controller through algorithms as that disclosed in "A corner-cube four-detector photopolarimeter," Optics and Laser Technology 29(5), 233–238 (1997), and "Polarization properties of corner-cube retroreflectors: theory and experiment," Applied Optics 36, 1553–1559 (1997) now incorporated as references in this Application.

Figure 3A:
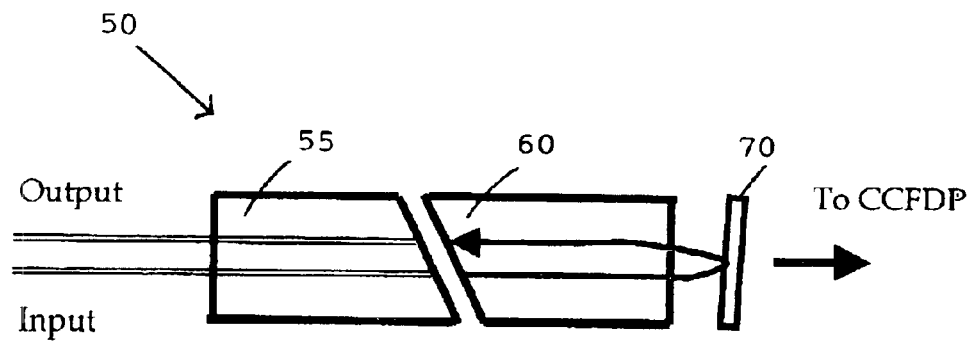
FIGS. 3A and 3B are cross sectional views of fiber tap coupling configuration for in-line Application of a corner cube four-detector photopolarimeter (CCFDPA) of this invention.
Figure 3B:
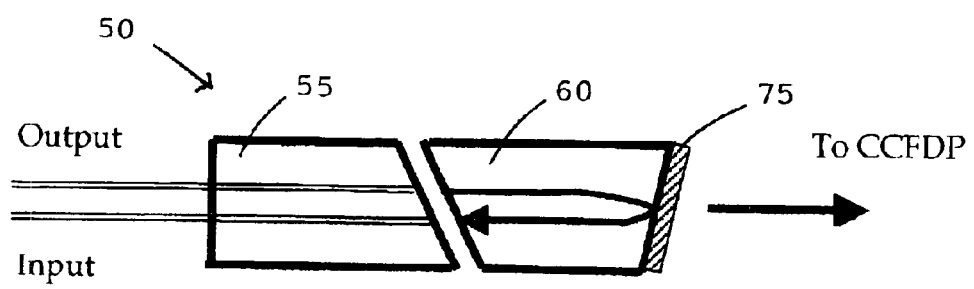

FIGS. 3A and 3B are two exemplary embodiments for coupling part of a corner cube four-detector photopolarimeter (CCFDPA) of this invention. As will be discussed below, this CCFDPA is compact in size and has a special advantage for implementing in an optical transmission system as the in-line photopolarimeter. A coupling optical signal tapping device 50 for tapping three to five percents (3–5%) of the optical signal is provided. The optical signal tapping device 50 includes a dual-core fiber pigtail 55 placed before a collimator 60, e.g., a GRIN lens, placed adjacent to an optical tap 70. A small portion of the optical signal is tapped for transmission to the CCFDP and majority of the optical signal is reflected back and outputted from the output fiber of the dual pigtail 55. In FIG. 3B, instead of a separate tap, a thin film coating 75 is coated at the output end of the collimator to tap the input signal into the CCFDP for state of polarization (SOP) characterization and reflect the majority of the light back to the other fiber of the dual-core fiber pigtail. With the tapping filter coated directly on the collimator, the overall size of the in-line CCFDP can be further reduced. The taping device 50 as shown can be polarization dependent or independent as its polarization properties can be calibrated. By integrating the CCFDP and the coupling structure shown in FIGS. 3A and 3B, the whole system becomes very compact to be conveniently implemented on many existing optical fiber network communication systems.

According to above descriptions, this invention discloses a optical signal transmission system. The optical signal transmission system includes an optical tap for tapping a small portion of optical signal from the optical signal transmission system. The optical signal transmission system further includes an inline corner-cube four-detector photopolarimeter (CCFDP) receiving the small portion of optical signal for measuring a state of polarization (SOP) of the optical signal and for generating electric signals corresponding to the SOP. And, the optical signal transmission system further an optical signal processor receiving the electric signals from the CCFDP for generating a polarization mode dispersion compensation signal for the optical signal transmission system. In a preferred embodiment, the CCFDP is a hollowed CCFDP comprising four optical detectors attached to four surfaces constituting a corner cube wherein at least one of surfaces receiving the portion of optical signal to project into the corner cube therein. In another preferred embodiment, the CCFDP is a solid CCFDP composed of optical transparent material wherein the CCFDP further comprising four optical detectors attached to four surfaces of a corner cube. In another preferred embodiment, each of the four optical detectors attached to the four surfaces of the corner cube with a coating of a specific refraction index and accurately controlled thickness for controlling an optical absorption for each of the detectors.

FIG. 4 is a perspective view of a solid corner cube four-detector photopolarimeter (CCFDP) 100 of this invention. This CCFDP 100 supported on a solid corner cube 110 with particular geometric arrangements of detectors and applying special coatings is suitable to operate for transmission of optical signals carried by optical signal channels near a 1550 nm window. By using a solid corner cube such as a glass corner cube, the detectors can be directly integrated on the surfaces of the solid corner cube to relax the alignment tolerance to significantly enhance the manufacturability of the four-detector photopolarimeter. By implementing a solid corner cube as a platform, the detectors are attached to the solid corner cube by applying transparent optical coatings. Special design considerations are incorporated in this invention by selecting the types of material to form the solid corner cube platform and the materials and the thickness of the coatings such that for a designated range of wavelengths, highly sensitive response of electric signals generated from absorption optical signal projected to the four detectors versus the variations of state of polarization (SOP) of the incident light is achieved. Azzam, R. A. and Giardina, K. A described some of these design considerations in a paper entitled "Achieving a given reflectance for unpolarized light by controlling the incidence angle and the thickness of a transparent thin film on an absorbing substrate: application to energy equipartition in the four-detector photopolarimeter" Applied Optics, 31, 935–942 (1992)). In one embodiment of this invention, the incidence angle is selected approximately fifty-four degrees (54°). In this invention, the material of the solid four corner cube is selected, e.g., a glass solid cube, and then the thickness and the material index of the coating is selected and controlled to achieve an optimal SOP measurement performance of the CCFDP.

The input light of unknown polarization and the input light has a wavelength within a range about a certain predefined wavelength, e.g., 1550 nm, is projected to four detectors sequentially. The four detectors are arranged such that the light is partially reflected and partially absorbed by the detectors. The electrical signals from the four detectors corresponding to the absorbed light are measured and then converted into the incoming state of polarization at a time of less than milliseconds (electronic processing time). As shown in FIG. 4, the first three detectors of the four detectors in this invention are attached to the outer surfaces of the solid corner-cube where these three surfaces are mutually perpendicular to each other. Since the optical path of the light and the detail arrangement of the detectors are well known, for the purpose of simplicity and clarity in describing the essence of this invention, the details will not be repeated here.

In one preferred embodiment, the corner cube is hollow corner cube and the first three detectors are attached to the inner surfaces of the corner cube with a attachment coating. Again, the position of the detectors can be calculated based on analyses provided in the prior art disclosures. Special coating is used for a hollow corner cube since the input medium is air. A specific thickness of transparent coating of a selected material is used to provide an optical measurement sensitivity that the variation of optical signal absorptions are most responsive to the variations of the state of polarization (SOP) with a predefined incident angle around a pre-selected range of wavelengths.

In another preferred embodiment, a solid corner cube is used as a platform to construct the photopolarimeter. The solid corner cube is composed of either glass or germanium or other optically transparent materials. The first three detectors are now placed on the outer surfaces of the corner cube by applying an epoxy with a specific thickness depending on the materials used for the solid corner cube. In one of the preferred embodiments, the thickness of the coatings applied to the first three detectors are selected to work for light with a wavelength approximately 1550 nm and the first three detectors when applied with the coatings are arranged to reflect a part of the incoming light while absorb the rest of the light. The absorbed light are received by the detector to generate a corresponding electric signal for a processor to determine the state of the polarization of the incident light. An alternate coating is a silicon nitride and this silicon nitride coating has a special advantage that the coating can be manufactured as part of the fabrication processes for the detectors. The thickness of these coatings is accurately controlled to optimize the measurement sensitivity. The fourth detector is employed to absorb the light. In one exemplary embodiment, the fourth detector has a coating thickness of one-quarter wavelength in thickness to absorb the light projected to the fourth detector. The fourth detector is specially arranged to have a certain small angle, e.g., five degrees, to the incoming light to avoid a reflection of the light back along the incident optical path. The fourth detector is attached to the solid corner cube by a fixture of an epoxy.

According to above descriptions, this invention discloses an optical polarization analyzer. The optical polarization analyzer includes a corner cube that includes four triangular surfaces each having an optical detector attached thereon wherein each of the detector further includes a coating coated over the detector and each of the coatings composed of a predetermined material and an accurately controlled thickness for controlling a detector absorption/reflectance ratio whereby an optimal photopolarimeter sensitivity is achieved. In a preferred embodiment, the corner cube is a hollowed corner cube wherein each of first three of the detectors are attached respectively to three inner surfaces by applying an optically transparent glue or epoxy type of surface attachment medium. In another preferred embodiment, the corner cube is a hollowed corner cube wherein each of first three of the detectors are attached respectively to three inner surfaces by applying an optical bonding process. In another preferred embodiment, the corner cube is a solid corner cube wherein each of four detectors are attached respectively to four outer surfaces by applying an optically transparent glue or epoxy type of surface attachment medium. In another preferred embodiment, the corner cube is a solid corner cube wherein each of four detectors are attached respectively to four outer surfaces by applying an optical bonding process.

This invention further discloses a method of designing an optical polarization analyzer for measuring a state of polarization (SOP) of an optical signal transmitted over a particular range of wavelengths. The method includes steps of selecting a corner cube having a specific input medium refraction index and comprising four triangular surfaces. The method further includes another step of attaching four optical detectors on each of the four surfaces for sequentially absorbing and then reflecting an incident light from one detector to a next detector wherein the incident light is within the particular range of wavelengths. And, the method further includes a step of selecting a coating to coat over each of the detectors disposed on each of the four surfaces by selecting a coating material and designing an accurately controlled thickness of each of the coatings for controlling a absorption/reflectance ratio for each of the detectors whereby an optimal photopolarimeter sensitivity is achieved. In a preferred embodiment, the step of selecting a corner cube is a step of selecting a hollow corner cube for attaching first three the detectors on three inner surfaces of the hollow corner cube applying a glue or epoxy type of surface attachment medium. In another preferred embodiment, the step of selecting a corner cube is a step of selecting a solid corner cube for attaching the detectors on four outer surfaces of the hollow corner cube applying a glue or epoxy type of surface attachment medium. In another preferred embodiment, the step of designing an optical polarization analyzer for measuring a state of polarization (SOP) of an optical signal transmitted over a particular range of wavelengths is a step of designing an optical polarization analyzer for measuring the SOP of an optical signal transmitted or a range of wavelengths approximately near a wavelength of 1550 nm.

Although the present invention has been described in terms of the presently preferred embodiment, it is to be understood that such disclosure is not to be interpreted as limiting. Various alternations and modifications will no doubt become apparent to those skilled in the art after reading the above disclosure. Accordingly, it is intended that the appended claims be interpreted as covering all alternations and modifications as fall within the true spirit and scope of the invention.

I claim:

1. An optical signal transmission system comprising:
   an optical tap for tapping a small portion of optical signal from the optical signal transmission system;
   an inline corner-cube four-detector photopolarimeter (CCFDP) receiving said small portion of optical signal for measuring a state of polarization (SOP) of said optical signal and for generating electric signals corresponding to said SOP; and
   an optical signal processor receiving said electric signals from said CCFDP for generating a polarization mode dispersion compensation signal for said optical signal transmission system; and
   said CCFDP is a hollowed CCFDP comprising four optical detectors attached to four surfaces constituting a corner cube wherein at least one of said surfaces receiving said portion of optical signal to project into said corner cube therein.

2. The optical signal transmission system of claim 1 wherein:
   said CCFDP is a solid CCFDP composed of optical transparent material wherein said CCFDP further comprising four optical detectors attached to four surfaces of the corner cube.

3. The optical signal transmission system of claim 2 wherein:
   each of said four optical detectors attached to said four surfaces of said corner cube is coated with a coating of a specific refraction index and with an accurately controlled thickness for controlling an optical absorption for each of said detectors.

4. The optical signal transmission system of claim 3 wherein:
   said thickness of said coating for each of said detectors are selected for working with an optical transmission of wavelength approximately 1550 nm.

5. The optical signal transmission system of claim 3 wherein:
   said thickness of said coating for said fourth detector has a thickness of approximately one-quarter wavelength.

6. The optical signal transmission system of claim 2 wherein:
   said solid corner cube is made of an optically transparent material.

7. The optical signal transmission system of claim 2 wherein:
   said solid corner cube is a glass solid corner cube.

8. The optical signal transmission system of claim 2 wherein:
   said solid corner cube is a germanium solid corner cube.

9. The optical signal transmission system of claim 2 wherein:
   said solid corner cube is a silicone solid corner cube.

10. The optical signal transmission system of claim 1 wherein:
    each of said four optical detectors attached to said four surfaces of said corner cube is coated with a coating of a specific refraction index and with an accurately controlled thickness for controlling an optical absorption for each of said detectors.

11. The optical signal transmission system of claim 10 wherein:
    said thickness of said coating for each of said detectors are selected for working with an optical transmission of wavelength approximately 1550 nm.

12. The optical signal transmission system of claim 10 wherein:
    said thickness of said coating for said fourth detector has a thickness of approximately one-quarter wavelength.

13. A method of compensating polarization mode dispersion in a optical signal transmission system comprising:
    employing an optical tap for tapping a small portion of optical signal from the optical signal transmission system;
    receiving said small portion of optical signal into an inline corner-cube four-detector photopolarimeter (CCFDP) for measuring a state of polarization (SOP) of said optical signal and for generating electric signals corresponding to said SOP;
    receiving said electric signals from said CCFDP into an optical signal processor for generating a dispersion compensation signal for said optical signal transmission system; and
    the step of receiving said small portion of optical signal into an inline CCFDP is a step of employing a hollowed CCFDP using four optical detectors attached to four surfaces constituting a corner cube to receive said portion of optical signal to project into said corner cube from one of said four surfaces.

14. The method of claim 13 wherein:
    the step of receiving said small portion of optical signal into an inline CCFDP is a step of employing a solid CCFDP composed of optical transparent material with four optical detectors attached to four surfaces a said corner cube.

15. An optical polarization analyzer comprising:
    a corner cube comprising four triangular surfaces each having an optical detector attached thereon wherein each of said detector further includes a coating coated over said detector and each of said coatings composed of a predetermined material and an accurately controlled thickness for controlling a detector absorption/reflectance ratio whereby an optimal photopolarimeter sensitivity is achieved.

16. The optical polarization analyzer of claim 15 wherein:
    said corner cube is a hollowed corner cube wherein each of first three of said detectors are attached respectively to three inner surfaces by applying an optically transparent glue or epoxy type of surface attachment medium.

17. The optical polarization analyzer of claim 15 wherein:

said corner cube is a hollowed corner cube wherein each of first three of said detectors are attached respectively to three inner surfaces by applying an optical bonding process.

18. The optical polarization analyzer of claim 15 wherein:

said corner cube is a solid corner cube wherein each of said four detectors are attached respectively to four outer surfaces by applying an optically transparent glue or epoxy type of surface attachment medium.

19. The optical polarization analyzer of claim 15 wherein:

said corner cube is a solid corner cube wherein each of said four detectors are attached respectively to four outer surfaces by applying an optical bonding process.

20. A method of designing an optical polarization analyzer for measuring a state of polarization (SOP) of an optical signal transmitted over a particular range of wavelengths comprising:

selecting a corner cube having a specific input medium refraction index and comprising four triangular surfaces;

attaching four optical detectors on each of said four surfaces for sequentially absorbing and then reflecting an incident light from one detector to a next detector wherein said incident light is within said particular range of wavelengths; and selecting a coating to coat over each of said detectors disposed on each of said four surfaces by selecting a coating material and designing an accurately controlled thickness of each of said coatings for controlling an absorption/reflectance ratio for each of said detectors whereby an optimal photopolarimeter sensitivity is achieved.

21. The method of claim 20 wherein:

the step of selecting a corner cube is a step of selecting a hollow corner cube for attaching first three of said detectors on three inner surfaces of said hollow corner cube by applying a glue or epoxy type of surface attachment medium.

22. The method of claim 20 wherein:

the step of selecting a corner cube is a step of selecting a solid corner cube for attaching said detectors on four outer surfaces of said solid corner cube by applying a glue or epoxy type of surface attachment medium.

23. The method of claim 20 wherein:

the step of designing an optical polarization analyzer for measuring a state of polarization (SOP) of an optical signal transmitted over a particular range of wavelengths is a step of designing an optical polarization analyzer for measuring said SOP of an optical signal transmitted over a range of wavelengths approximately near a wavelength of 1550 nm.

* * * * *